US012544260B2

(12) United States Patent
Kuebler et al.

(10) Patent No.: US 12,544,260 B2
(45) Date of Patent: Feb. 10, 2026

(54) METHOD FOR OPERATING A FLUID PUMP, AND OPHTHALMIC SURGICAL SYSTEM WITH SAME

(71) Applicant: Carl Zeiss Meditec AG, Jena (DE)

(72) Inventors: Christoph Kuebler, Oberkochen (DE); Susanne Kohlhammer, Blaustein (DE)

(73) Assignee: Carl Zeiss Meditec AG, Jena (DE)

( * ) Notice: Subject to any disclaimer, the term of this patent is extended or adjusted under 35 U.S.C. 154(b) by 569 days.

(21) Appl. No.: 17/950,061

(22) Filed: Sep. 21, 2022

(65) Prior Publication Data

US 2023/0086987 A1 Mar. 23, 2023

(30) Foreign Application Priority Data

Sep. 21, 2021 (DE) ..................... 10 2021 124 415.3

(51) Int. Cl.
*A61F 9/007* (2006.01)

(52) U.S. Cl.
CPC ... *A61F 9/00736* (2013.01); *A61M 2205/123* (2013.01)

(58) Field of Classification Search
CPC .. A61F 9/00736; A61F 9/00745; A61F 9/007; A61M 2205/123; A61M 1/74; A61M 1/73; A61M 2205/3317; A61M 3/0216; A61M 2205/3341; A61M 1/77; A61M 1/72; A61M 3/0201; A61M 3/0258; A61M 2210/0612; A61M 2205/0272;
(Continued)

(56) References Cited

U.S. PATENT DOCUMENTS 4,775,470 A * 10/1988 Zook .................. A61M 1/1639 210/321.71
10,722,619 B2 7/2020 Kuebler et al.
(Continued)

FOREIGN PATENT DOCUMENTS

DE 3716765 A1 11/1987
DE 102016201297 B3 3/2017

OTHER PUBLICATIONS

European Search Report dated Feb. 10, 2023 of European counterpart application No. 22195884.6 and English Language Translation thereof.

(Continued)

*Primary Examiner* — Nicholas J. Weiss
*Assistant Examiner* — Brandon W. Levy
(74) *Attorney, Agent, or Firm* — Ewers IP Law PLLC; Falk Ewers

(57) ABSTRACT

A cartridge for a panel of an ophthalmic surgical system for treating an eye is configured for insertion in a cartridge accommodation region of the panel and has at least one fluid pump for conveying a treatment fluid, the fluid pump has a pump chamber and a drive chamber separated from the pump chamber with a partition element that is at least regionally deflectable, wherein a drive fluid is feedable to the drive chamber and the treatment fluid is feedable to the pump chamber. The partition element has at least one plate element made of an at least electrically conductive or at least ferromagnetic material, said plate element also being deflected in the case of a deflection of at least one region of the partition element. Further, a panel and an ophthalmic surgical system are provided.

8 Claims, 4 Drawing Sheets

(58) Field of Classification Search
CPC ............ A61M 2205/6054; A61M 1/80; A61B 2217/005; A61B 2217/007
See application file for complete search history.

(56) References Cited

U.S. PATENT DOCUMENTS

| | | | | |
|---|---|---|---|---|
| 2004/0265150 | A1* | 12/2004 | McElfresh | B81B 3/0035 251/129.01 |
| 2013/0303978 | A1 | 11/2013 | Ross | |
| 2017/0216093 | A1* | 8/2017 | Kuebler | A61M 3/0216 |
| 2020/0353133 | A1 | 11/2020 | Gao et al. | |
| 2021/0093482 | A1 | 4/2021 | Mehta | |

OTHER PUBLICATIONS

Office Action issued in German Patent Application No. DE 10 2021 124 415.3, dated May 23, 2022 (from which this application claims priority) and English language translation thereof.
www.wikipedia.de "Wegesensor" Version vom 21.06.2021 and English language translation thereof.

* cited by examiner

METHOD FOR OPERATING A FLUID PUMP, AND OPHTHALMIC SURGICAL SYSTEM WITH SAME

CROSS REFERENCE TO RELATED APPLICATIONS

This application claims priority to German patent application 10 2021 124 415.3, filed Sep. 21, 2021, the entire content of which is incorporated herein by reference.

TECHNICAL FIELD

The disclosure relates to a cartridge for a panel of an ophthalmic surgical system for treating an eye, the cartridge being configured for insertion in a cartridge accommodation region of the panel and having at least one fluid pump for conveying a treatment fluid, the fluid pump having a pump chamber and a drive chamber separated from the pump chamber by way of a partition element that is at least regionally deflectable, with a drive fluid being feedable to the drive chamber and the treatment fluid being feedable to the pump chamber. Further, the disclosure includes a panel of an ophthalmic surgical system for treating an eye, at least including a cartridge accommodation region for accommodating a cartridge having at least one fluid pump for conveying a treatment fluid, the fluid pump having a pump chamber and a drive chamber separated from the pump chamber by way of a partition element that is at least regionally deflectable, with a drive fluid being feedable to the drive chamber and the treatment fluid being feedable to the pump chamber, a drive fluid supply system for feeding the drive fluid into the drive chamber, and a sensor unit for detecting a deflection position of the partition element. The disclosure finally also relates to an ophthalmic surgical system for treating an eye.

BACKGROUND

Ophthalmic surgical systems, panels therefor, and cartridges for insertion in panels are known in the related art, and so in principle there is no need for separate documentary evidence in this respect. Various surgical techniques are known for treatment of a clouding of the crystalline lens, also known in medicine as cataract. The most widespread technique is phacoemulsification, in which a thin hollow needle is introduced into a capsular bag, in which the crystalline lens is arranged, and is induced to make ultrasonic vibrations. The lens can be emulsified with the vibrating hollow needle, and lens particles released in the process can be aspirated through an aspiration line with a pump. In the process, an irrigation fluid is supplied. The lens particles are aspirated, together with the fluid, as aspiration fluid. As soon as the lens has been completely emulsified and removed, a new artificial lens can be inserted into the then empty capsular bag. The treated patient can in this way recover good vision.

An advanced ophthalmic surgical system that has proven particularly suitable for phacoemulsification is described in DE 10 2016 201 297 B3, for example. In this system, two fluid pumps fluidically connected in parallel are used in each case for the irrigation and also for the aspiration. Each of the fluid pumps has a pump chamber, and a drive chamber separated from the pump chamber with a partition element. For the intended operation of the fluid pump, the drive chamber is acted upon by a drive fluid whose drive pressure is varied for performing a respective pump stroke. Depending on this, a deflection position of the partition element thus changes, which has a corresponding effect on the pump chamber. The pump chamber is acted upon by the respective treatment fluid, for example the irrigation fluid, the aspiration fluid or the like. The delivery action can then be achieved by suitably controlling an inlet valve and an outlet valve of the fluid pump.

A deflection position of the partition element is detected with a deflection position sensor assigned to the respective fluid pump. A control device of the ophthalmic surgical system, in particular of the panel, controls the function of the fluid pump at least depending on a sensor signal of the deflection position sensor and on a drive pressure signal supplied with a drive pressure sensor. In addition, the control device can, for example, control the inlet valve and the outlet valve accordingly.

By alternate actuation of the respective two fluid pumps connected in parallel, a volumetric flow with very little fluctuation can be obtained during a surgical procedure. In this way, an almost constant intraocular pressure can be obtained in the capsular bag. As long as sufficient irrigation fluid can be delivered, the system can also be operated almost without interruption of the flow of irrigation fluid, even during a very protracted surgical procedure.

The partition element of a respective one of the fluid pumps is thus not actuated by a plunger or a rod but instead by the drive fluid. It is thus possible to achieve almost jolt-free and very rapid actuation. At the same time, the fluid pump embodied in this manner proves very reliable and requires very little maintenance. The ophthalmic surgical system described in DE 10 2016 201 297 B3 is therefore also particularly suitable for a method implementation that requires a reaction to a blockage of a needle tip of the hollow needle or of the aspiration opening. Such a state is also referred to as occlusion. With the ophthalmic surgical system proposed in DE 10 2016 201 297 B3, this situation can also be handled very effectively, and so an intraocular pressure can be kept almost constant even in the event of such operating disturbances.

For the intended operation of the ophthalmic surgical system, it is desirable to keep the intraocular pressure, in particular in the capsular bag, as constant as possible by regulating the pressure of the irrigation fluid and of the vacuum of the aspiration fluid. For this purpose, it is desirable that the pressure of the treatment fluid be known as precisely as possible, so that correspondingly precise regulation of this pressure can be achieved.

In the previously described fluid pump, the pressure of the treatment fluid depends on the drive pressure of the drive fluid. In addition, there is also a dependency on properties of the partition element. Deviations in properties between different partition elements may occur on account of component fluctuations and tolerances and also ageing effects resulting from storage or the like. These deviations may, for example, concern a dependency of a pressure difference, brought about by the partition element, on a respective deflection position of the partition element. Such a deviation may lie above a desired precision range that is expedient for the regulation of the intraocular pressure. Overall, it is desirable to know the defection position of the partition element as accurately as possible, in order to be able to determine, inter alia, the pressure of the treatment fluid therefrom. In this context, DE 37 16 765 A1 describes a membrane with a magnet. Further, US 2004/0265150 A1 describes a magnetic membrane system.

SUMMARY

It is therefore an object of the disclosure to improve a cartridge, a panel and an ophthalmic surgical system such that the deflection position of the partition element can be detected in improved fashion, in particular for control in relation to the treatment fluid.

The object is achieved by a cartridge for a panel of an ophthalmic surgical system for treating an eye, a panel of an ophthalmic surgical system for treating an eye, and an ophthalmic surgical system for treating an eye as described herein.

In relation to a generic cartridge for a panel of an ophthalmic surgical system for treating an eye, the disclosure provides in particular that the partition element has at least one plate element made of an at least electrically conductive or at least ferromagnetic material, said plate element also being deflected in the case of a deflection of at least one region of the partition element.

In relation to a generic panel of an ophthalmic surgical system for treating an eye, the disclosure provides in particular that the sensor unit is configured to use a magnetic field to detect a deflection position of the plate element which is part of a cartridge according to an aspect of the disclosure and arranged on the partition element.

In relation to a generic ophthalmic surgical system for treating an eye, the disclosure provides in particular that at least the cartridge is configured according to an aspect of the disclosure or the panel is configured according to an aspect of the disclosure.

The disclosure is based, inter alia, on the concept that the function of the regulation for the treatment fluid can be improved if the properties of the fluid pump are known better and more precisely. This applies in particular to the deflection position of the partition element. Since the fluid pump generally serves to convey a medical treatment fluid, reasons of hygiene and reasons of sustainability often mean that no pressure sensors are provided for the treatment fluid. A conclusion regarding the pressure of the treatment fluid can therefore only be reached indirectly in such a case, that is to say depending on, inter alia, the drive pressure of the drive fluid. By contrast, the actual pressure of the treatment fluid need not be measured. Therefore, detecting the specific deflection position of the partition element as accurately as possible and using this for the control of the fluid pump is desirable. The control function can be realized more accurately and hence also more purposefully as a result of the structure according to an aspect of the disclosure of the cartridge, especially in conjunction with the panel.

To this end, the deflection position of the partition element is detected with the deflection position sensor in the panel when the cartridge is arranged in the panel. For this purpose, the partition element has the plate element, which may be in the form of a metal plate, for example. The plate element can have a flat, typically planar, panel-shaped embodiment. It may have an edge all around, which may be at least partly round or polygonal in form. However, the plate element may also have a given curvature in the plane, for example in order to be able to assist a contour of the partition element, especially during intended use. The plate element typically has two opposing large surfaces, with one of the surfaces being able to be connected to a surface of the partition element. The plate element is typically arranged at a surface of the partition element that faces the drive chamber.

As a result of the partition element having at least one electrically conductive material or at least one ferromagnetic material, it is possible to use a magnetic field to detect the position of the plate element and hence the deflection position of the partition element. To this end, the panel has the sensor unit, which is typically configured as an inductive sensor unit, which provides a suitable magnetic field and which detects properties of the magnetic field that are dependent on the position of the plate element. On the basis of the detected magnetic field, the sensor unit can provide a sensor signal which can be fed to a control device of the panel in order to determine the deflection position of the partition element by evaluating the sensor signal. Should the material of the plate element be ferromagnetic, provision can be made for the sensor unit to use a substantially constant magnetic field for the detection of the deflection position. However, an alternating magnetic field may also be provided, depending on the configuration. By contrast, only an alternating magnetic field may typically be provided if the material of the plate element is only electrically conductive. Of course, combinations of these may also be provided. The partition element itself has a fluid-tight and ion-tight embodiment, in particular. As a result, a substance-tight separation between the pump chamber and the drive chamber can be obtained.

The disclosure therefore enables contactless determination of the deflection position of the partition element. The disclosure can be realized with little outlay by virtue of the sensor unit being arranged in the panel and the plate element only needing to be provided in the cartridge in supplementary fashion. The expense due to the plate element for the cartridge generally realized as a replaceable disposable part is comparatively low. By contrast, the sensor unit arranged in the panel can be used multiple times, and so overall the additional expense can also be kept low here. The cartridge is typically formed without a sensor unit.

The partition element, which separates the pump chamber from the drive chamber, can be configured as an elastic partition element in the manner of an elastic membrane, a film or the like. Moreover, the partition element may also have, at least regionally, a substantially rigid exemplary embodiment, with typically the rigid region being displaceable. Furthermore, the partition element may have an edge, for example, with which it can be securely connected to the fluid pump. By way of example, at its edge, the partition element might not be displaceable in an axial direction that runs parallel to a partition element center axis. In particular, provision can be made for the partition element to be securely clamped at its edge. Typically, a circumferential edge of the partition element can be arranged or secured fixedly in the fluid pump. In this way, the partition element can fluidically separate the pump chamber from the drive chamber, particularly in such a way that a sterility of the treatment fluid is not impaired.

The fluid pump is, inter alia, completely taken hold of by the cartridge. As a result, the cartridge can be detachably connected to the panel, with, in the connected state and as a result of the drive chamber being connected to the drive fluid supply system of the panel, the fluid pump being able to be fluidically coupled for the purposes of feeding a drive fluid to the drive chamber. In the panel-connected state of the cartridge, the sensor unit can be positioned in the region of the fluid pump of the cartridge such that a reliable function can be ensured.

With the cartridge, therefore, a replacement part or disposable part can be made available which can serve to ensure a sterility of the ophthalmic surgical system for a respective surgical procedure on the eye, particularly as regards the treatment fluid. This is because the treatment fluid only needs to be fed through the cartridge as a result, and so the treatment fluid need not flow through the panel and also need not come into contact with the panel. In this way, after a respective use of the ophthalmic surgical system, it is easily possible to restore the sterility of the ophthalmic surgical system by replacing the cartridge in the panel.

Naturally, in the panel-connected state, provision is made for the cartridge to be connected in fluid-tight fashion to the panel such that the respective drive chamber of the respective fluid pump can be coupled to the drive fluid supply system in fluid-tight fashion in order to be able to operate the fluid pump as intended. By way of example, provision can be made that the cartridge, in particular also the fluid pump or the cartridge-side elements of the fluid pump, in particular the respective partition element, can be produced from a suitable plastic or comparable material.

The drive fluid, which is feedable to the drive chamber in order to be able to drive the fluid pump, can be for example a liquid, such as for example water, oil, mixtures of liquids and/or the like, and also a gas, for example air, nitrogen, a noble gas, mixtures of gases and/or the like, and also a combination of these.

The drive fluid can typically be made available exclusively with the panel. For this purpose, for example, the drive fluid supply system in the panel can have a drive pressure sensor, with which the drive pressure of the drive fluid can be detected. By virtue of the fact that the drive pressure sensor can be provided at the panel side, and because it does not need to come into contact with the treatment fluid, it does not have to meet any particular requirements as regards sterility. Therefore, the drive pressure sensor can be chosen and optimized in terms of its detection functionality.

Furthermore, the sensor unit is provided panel-side and serves to detect the deflection position of the partition element. The sensor unit can detect the deflection position of the partition element typically in a contactless manner. To this end, the sensor unit may have an inductive sensor element, for example. The sensor unit can communicate with a control device of the ophthalmic surgical system, in particular of the panel, by cable or wirelessly, for example by radio, or also via a communication line. By way of example, the sensor unit can be configured as a transponder, in particular as a passive transponder.

The plate element may have a round and/or a polygonal contour. It typically has a substantially planar or flat form. However, the plate element may also have an at least partially curved form in alternative configurations. The plate element typically has a substantially rigid embodiment such that it hardly deforms or substantially does not deform during intended operation. As a result, the plate element can provide the partition element with additional stability in relation to the deformation. The plate element may also have a multi-part design, for example have a layered construction or the like. Moreover, the plate element may be at least partly formed from a resilient substance.

The cartridge may have a cartridge housing, which may be formed from a suitable material, for example a plastic or the like. The fluid pump may be designed integrally with the housing at least in part.

Furthermore, it is provided that the plate element has a thickness smaller than a thickness of the partition element. As a result, the plate element may for example also be arranged integrated in the partition element. By way of example, the plate element can be surrounded by a material of the partition element, for example by being insert-molded.

Moreover, the plate element is arranged at a distance from an edging that holds the partition element. The edging may be provided by a housing of the cartridge and for example have a groove, in which an edge of the partition element is fastened. The edging is typically configured such that it is possible to realize a fluid-tight separation between the drive chamber and the pump chamber. The plate element is arranged at a distance from the edging such that the fluid-tight separation is not impaired as far as possible. The edging can realize a cohesive connection of a housing of the cartridge to the partition element. Moreover, provision can naturally also be made for the edging to include sealing means which, in addition to a fluidic seal, may also provide a holding function for the partition element. However, a press-fit connection may also be provided. Moreover, provision can naturally also be made for the partition element to have an integral form together with the edging and the housing of the cartridge.

On the drive chamber side, the partition element has an accommodation region, in particular a central accommodation region, for arranging the plate element. What can be achieved as a result of the accommodation region is that the plate element, as a separate part, can be connected to the partition element. Consequently, the partition element and the plate element can be produced separately from one another. By way of example, the accommodation region can be formed by a pocket which is provided by the partition element, in particular on the drive chamber side. The plate element can be inserted into the accommodation pocket during the production of the cartridge. The accommodation region typically has a form adapted to accommodating the plate element. It has been found to be particularly advantageous if the accommodation region is arranged centrally in relation to an extent of the partition element. As a result, the plate element can be arranged substantially centrally in relation to the partition element, as a result of which the function of the fluid pump can be assisted.

Moreover, a ring region extends around the accommodation region of the partition element in the circumferential direction. What this can achieve is that at least a portion of the partition element remains elastically movable in the circumferential direction, for example in the region of the edging, in order to be able to reliably realize the pump function. What can be achieved at the same time, especially if the accommodation region is arranged centrally, is that a reduced elasticity can be realized in a central portion of the partition element as a result of the plate element, as a result of which the deflection position can be better defined and can be better detected with the sensor unit. Typically, the ring region has a substantially constant radius in the circumferential direction. The partition element is in the form of a plate.

The plate element can be arranged on, in particular fastened to, a surface of the partition element, typically on the drive chamber side. By way of example, the plate element can be fastened to the surface of the partition element with an adhesive bond connection, a welded connection or the like. The low thickness of the plate element moreover allows the plate element to have a low weight such that the function of the fluid pump, in particular of the partition element during the intended operation of the fluid pump, is impaired as little as possible, typically substantially not impaired at all.

It is further provided that the plate element has a coating. The coating may serve to protect the plate element from interactions with the partition element and/or the drive fluid. By way of example, the coating may therefore provide a passivating effect. By way of example, the coating may be formed by a resin, a plastic or the like, which is applied to a surface of the plate element or all surfaces of the plate element. However, in principle the coating may also be a chemical layer which realizes a passivating effect, for example in the case of a plate element made of aluminum in conjunction with a work fluid made of air, wherein an aluminum oxide layer may form on the surface of the plate element as a coating.

Further, it is provided that the partition element have at least one connection element located on the drive chamber side and serving for the mechanical connection of the plate element arranged in the accommodation region to the partition element. The connection element typically allows the plate element to be detachably connected to the partition element. This is a particularly advantageous should the cartridge be realized as a disposable part or a single-use part and material separation is intended to be provided for recycling purposes. Moreover, a simple assembly of the plate element on the partition element can be achieved by way of the connection element. By way of example, the connection element can mechanically connect the plate element to the partition element at definable positions. However, it may also be provided as a single part which holds the plate element.

Further, the at least one connection element is provided to have at least one receiving groove for an edge of the plate element. What this can achieve is that the plate element can be connected to the partition element by pushing or clipping the edge into the receiving groove. This enables a simple assembly which, at the same time, also allows the realization of a sufficient sterility.

The ophthalmic surgical system for treating an eye has at least one panel for receiving a treatment fluid container for receiving a treatment fluid. For example, the treatment fluid container can be an irrigation fluid container which has a sufficiently large capacity for an irrigation fluid to ensure that even a somewhat lengthy surgical procedure can be carried out without replacing the treatment fluid container. In principle, the same can also be provided for a treatment fluid container which serves to receive the aspiration fluid. Moreover, the ophthalmic surgical system has the cartridge, insertable into the panel, for steering the treatment fluid to the surgical instrument for treating the eye. The cartridge is typically configured such that the treatment fluid does not come into contact with the panel. The cartridge can be configured as a disposable part, such that, after it has been used in a surgical procedure on an eye, it can be replaced for a subsequent surgical procedure. Sterility can thus be produced in a simple way. Moreover, the ophthalmic surgical system has at least one fluid pump for conveying the treatment fluid in the intended operation of the system, the fluid pump typically being arranged in the cartridge. Typically, at least one fluid pump is provided for conveying the irrigation fluid and at least one pump is provided for conveying the aspiration fluid. Each fluid pump has a pump chamber, and a drive chamber separated from the pump chamber with the partition element. The drive chamber can be acted upon by the drive fluid, which can be delivered to the drive chamber on the panel side. For this purpose, a source of drive fluid can be provided that is configured to be adjustable in terms of the drive pressure. The drive pressure can be detected with a drive pressure sensor, which likewise can be arranged on the panel side. With this exemplary embodiment of the fluid pump, it is possible that the treatment fluid can be guided in the cartridge substantially separate from the panel. Only attachments for delivery of the treatment fluid to the fluid pump and for removal of the treatment fluid from the fluid pump need to be provided on the cartridge.

The ophthalmic surgical system further includes a sensor unit for detecting the deflection position of the partition element. The sensor unit is typically arranged panel side. For communication purposes, the sensor unit can typically be coupled wirelessly to the control device, in particular to the ophthalmic surgical system control device arranged typically in the panel.

The panel can additionally have the control device which can realize the required functions for the intended operation and also in particular for the method implementations according to an aspect of the disclosure. For this purpose, the control device can be attached to the corresponding sensors and drive and control elements.

The advantages and effects specified for the cartridge according to an aspect of the disclosure and the panel according to an aspect of the disclosure naturally also equally apply to the ophthalmic surgical system according to an aspect of the disclosure, and vice versa.

Further features of the disclosure are evident from the figures and the description of the figures. The features and combinations of features mentioned in the description above and the features and combinations of features mentioned in the description of the figures hereinbelow and/or shown only in the figures may be used not only in the respectively specified combination but also in other combinations, without departing from the scope of the disclosure. Hence, exemplary embodiments of the disclosure which are not explicitly shown and explained in the figures, but which emerge and are producible by way of separated combinations of features from the explained exemplary embodiments, should also be considered to be encompassed and disclosed. Disclosure shall also be considered to extend to configurations and combinations of features that thus do not have all the features of an independent claim as originally worded. In addition, disclosure shall be considered to extend to configurations and combinations of features, especially via the configurations set out above, that go beyond or depart from the combinations of features set out in the dependency references of the claims.

BRIEF DESCRIPTION OF THE DRAWINGS

The disclosure will now be described with reference to the drawings wherein.

DESCRIPTION OF EXEMPLARY EMBODIMENTS

Figure 1:
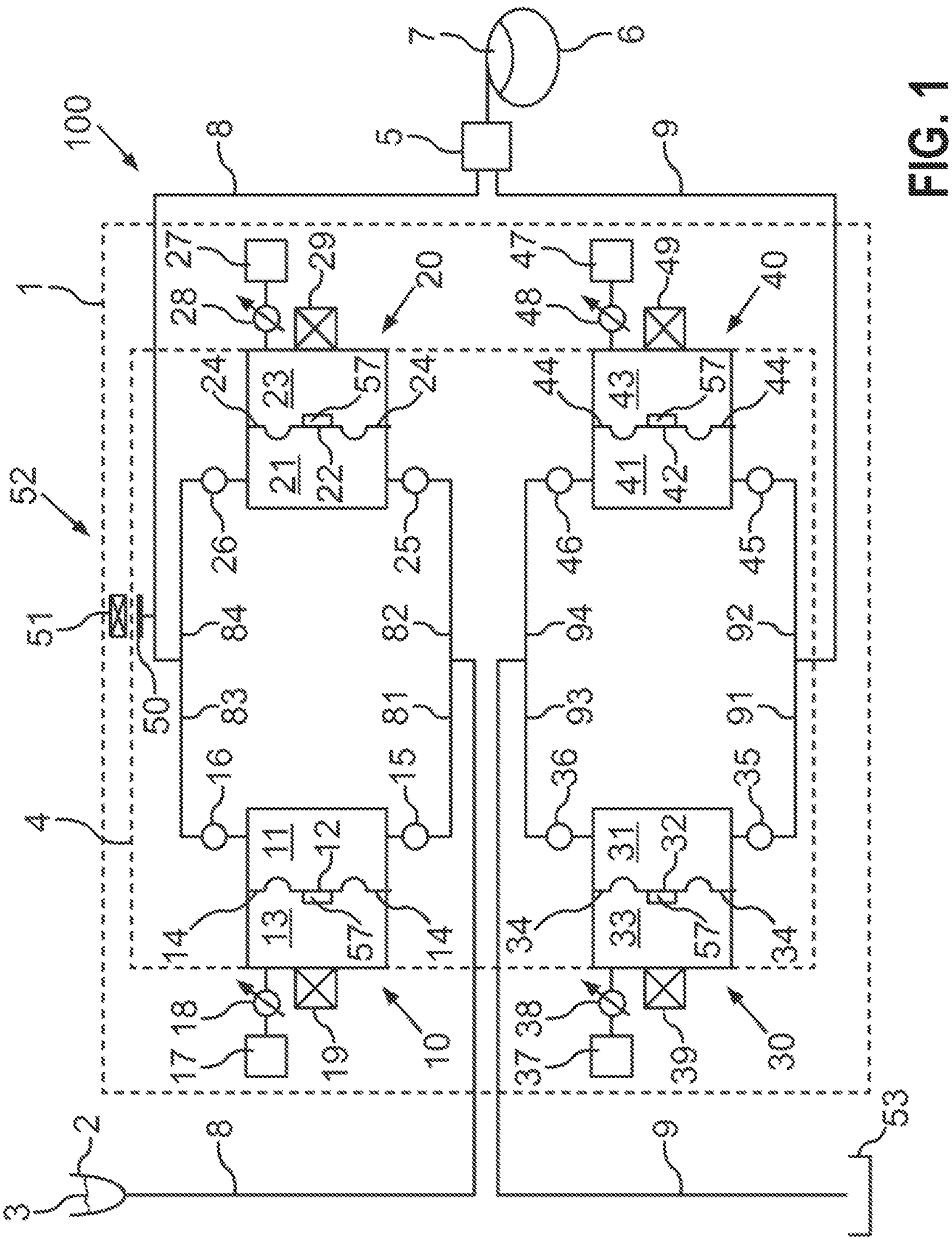
FIG. 1 shows a schematic illustration of the ophthalmic surgical system according to a first exemplary embodiment of the disclosure.
Figure 2:
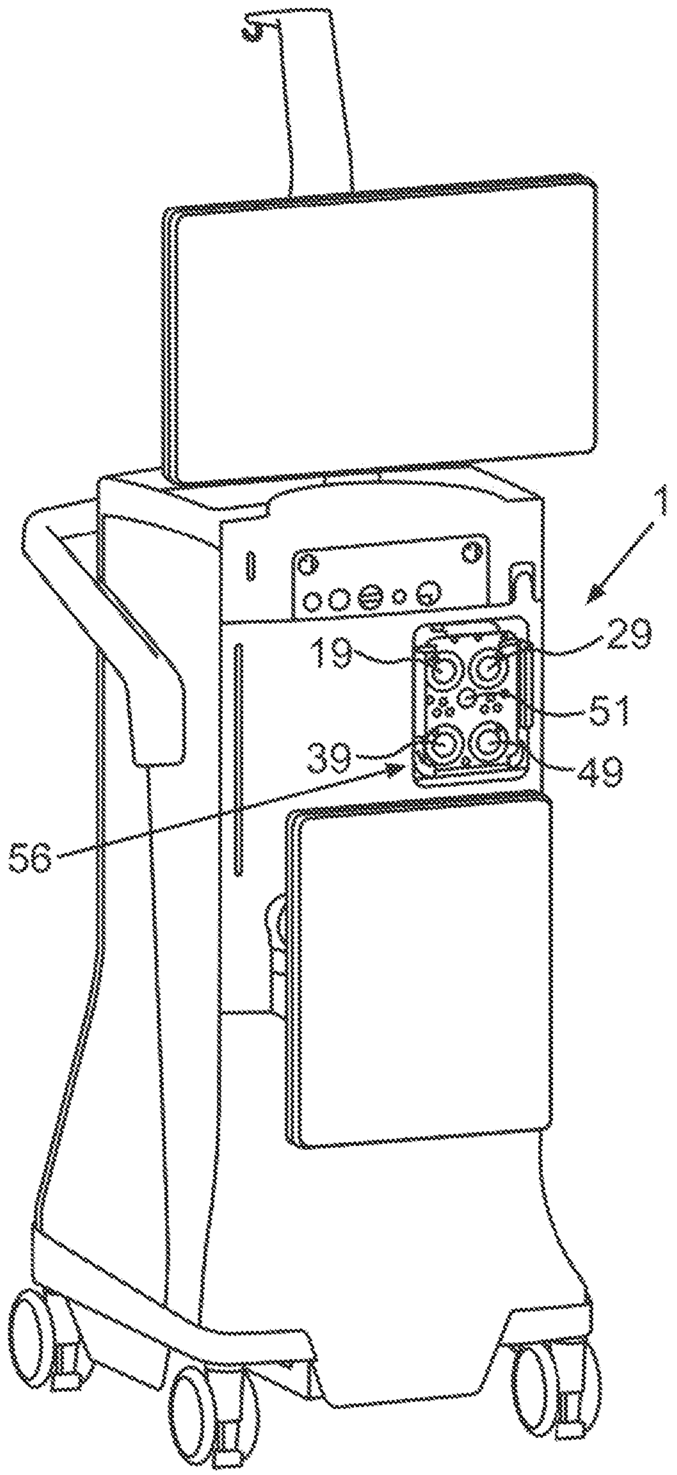
FIG. 2 shows a schematic perspective illustration of a panel of the system according to FIG. 3 shows a schematic plan view of a connection side of a cartridge for the system according to FIG. 1.
Figure 3:
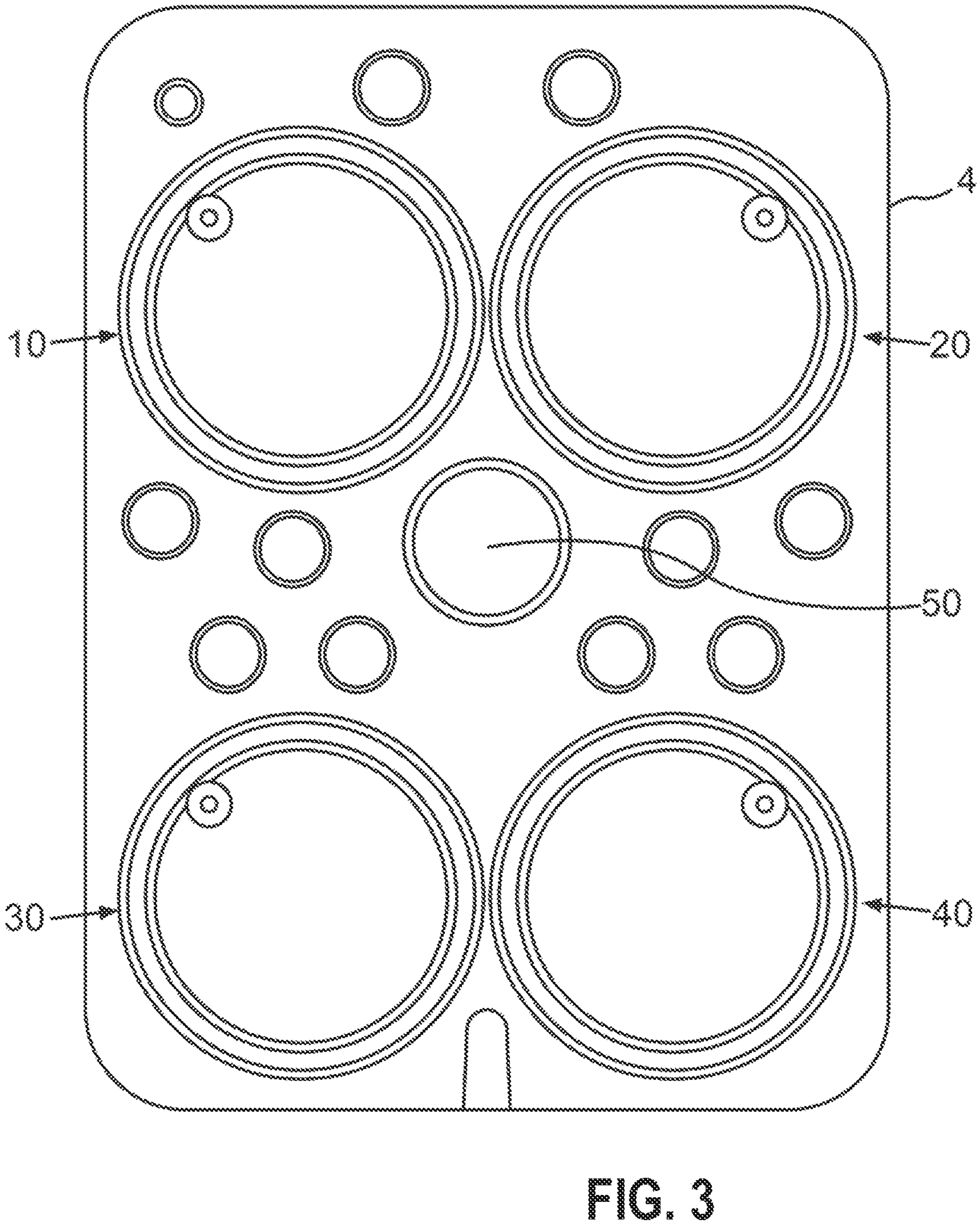

FIG. 1 shows a schematic illustration of a first embodiment of an ophthalmic surgical system 100 according to the disclosure. The system 100 has a panel 1, to which an irrigation fluid container 2 with an irrigation fluid 3 present therein is coupled. In addition, the system 100 has a cartridge 4 which is insertable into the panel 1. In addition to conveying the irrigation fluid 3 to a surgical instrument 5 as a medical treatment instrument, which serves for phacoemulsification of a lens 7 in an eye 6 as a treatment, the cartridge 4 also serves to remove an aspiration fluid, arising in the process, from a treatment region of the eye 6. In the present case, the surgical instrument 5 is in the form of a handpiece and serves for phacoemulsification of the lens 7 in the eye 6. FIG. 2 shows a schematic perspective illustration of the panel 1 without the cartridge 4. FIG. 3 shows a schematic plan view of an attachment side of the cartridge 4 for connection to the panel 1.

The system 100 further includes an irrigation fluid flow path 8, which runs from the irrigation fluid container 2 to the surgical instrument 5 via the cartridge 4. In addition, the system 100 has a first fluid pump 10 with a first pump chamber 11, and a first drive chamber 13 separated therefrom by a first partition element 12. The partition element 12 typically has a deformable embodiment. The first partition element 12 has an edge 14, with which it is fixedly connected in the fluid pump 10. At its edge 14, the partition element 12 is not displaceable in an axial direction that runs parallel to a partition element center axis. The partition element 12 is typically securely clamped at its edge 14.

The irrigation fluid 3 can be delivered to the first pump chamber 11 via the irrigation fluid flow path 8 and a first inlet valve 15 of the first pump chamber 11, depending on a valve state of the inlet valve 15. Moreover, it can be removed from the pump chamber 11 again via an outlet valve 16, depending on the valve state of the latter. The first drive chamber 13 can be acted upon by a first drive fluid 17, which can be delivered with a proportional valve 18 arranged in the panel 1. Depending on a differential pressure between the first drive fluid 17 in the first drive chamber 13 and the irrigation fluid 3 as treatment fluid in the first pump chamber 11, there is a regional deflection of the first partition element 12. A magnitude of the pressure in the first drive chamber 13 is greater than a magnitude of the pressure in the first pump chamber 11. When the inlet valve 15 is closed and the outlet valve 16 is open, the irrigation fluid 3 can flow out of the first pump chamber 11 into a subsidiary path 83 attached to the outlet valve.

A deflection position of the first partition element 12 can be detected with a first deflection position sensor 19, which is arranged outside the first fluid pump 10, for example in the panel 1. In the present case, the first deflection position sensor 19 is in the form of a sensor unit in the style of an inductive position encoder. The function of the deflection position sensor 19 will be explained further below.

As is evident from FIG. 1, the drive chamber 13 and the pump chamber 11 with the partition element 12 are arranged in the cartridge 4. As a result, the fluid pump 10 is coupled to a drive fluid feed of the panel 1 and to the deflection position sensor 19 arranged in the panel 1 as a result of arranging the cartridge 4 in the panel 1, and so it is possible to obtain the desired pump function and the detection function for detecting the deflection position of the first partition element 12.

It is also evident from FIG. 1 that a second fluid pump 20 is fluidically connected in parallel to the fluid pump 10. In the present case, the fluid pump 20 is configured like the fluid pump 10. Therefore, the irrigation fluid flow path 8 in the cartridge 4 is divided into a first subsidiary path 81 and a second subsidiary path 82. The first subsidiary path 81 is attached to the first inlet valve 15, and the second subsidiary path 82 is attached to a second inlet valve 25 of the second fluid pump 20.

The second fluid pump 20 has a second pump chamber 21, and a second drive chamber 23 separated from the latter with a second partition element 22. The partition element 22 has a second edge 24, which is mounted fixedly in the second fluid pump 20. The second drive chamber 23 can be acted upon by a second drive fluid 27 via a second proportional valve 28 arranged in the panel 1. A deflection position of the partition element 22 can be detected with a deflection position sensor 29, which in the present case is formed in accordance with the deflection position sensor 19. By way of a second outlet valve 26, the irrigation fluid 3 can again leave the second pump chamber 21 into the subsidiary path 84. By way of the subsidiary paths 83, 84, which are attached to the first and second outlet valve 16, 26 respectively, the irrigation fluid leaving the respective fluid pump 10, 20 can be delivered again to the irrigation fluid flow path 8, in order to be delivered to the instrument 5.

Figure 4:
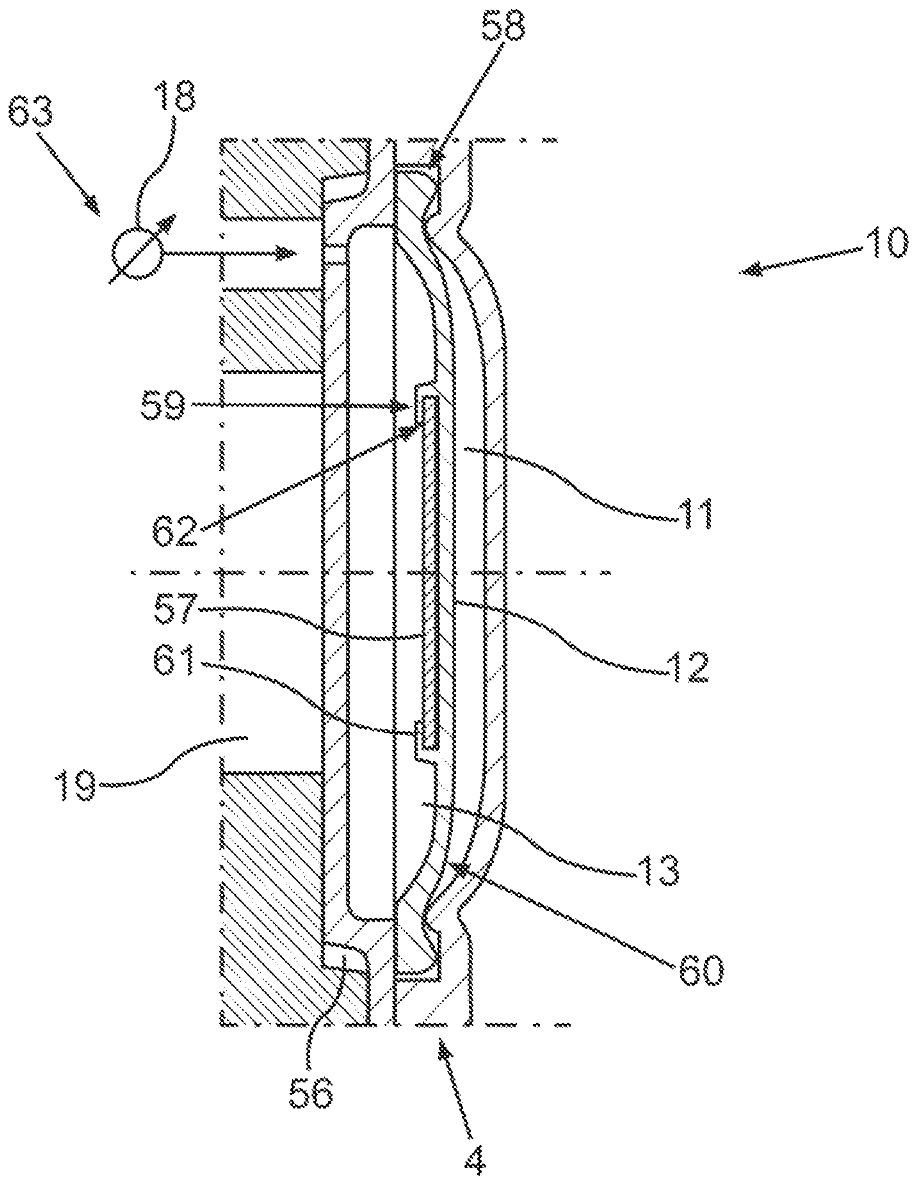
FIG. 4 shows a schematic sectional representation of a section of the cartridge according to FIG. 3 arranged in a cartridge accommodation region of the panel according to FIG. 2.

In a region of the fluidic connection of the subsidiary path 83 to the subsidiary path 84, i.e., for example in the downstream irrigation fluid flow path 8, an elastic membrane 50 is formed which can contact the irrigation fluid 3. The membrane 50 is arranged at the cartridge 4. The membrane 50 is contacted by a force sensor 51, which for its part is arranged in the panel 1 when the cartridge 4 is arranged in the cartridge accommodation region 56 (FIG. 4). The membrane 50, in conjunction with the force sensor 51, forms a detection sensor 52.

During the comminution of the crystalline lens 7, small lens particles are released and can be aspirated together with the delivered irrigation fluid. The irrigation fluid, contaminated with lens particles, is then referred to as aspiration fluid and is conveyed via an aspiration fluid flow path 9 to an aspiration fluid collection container 53. For this purpose, two further fluid pumps 30, 40 connected in parallel are presently provided which, in principle, are embodied comparably to the fluid pumps 10, 20 for the irrigation fluid. For this purpose, provision is made inside the cartridge 4 that the aspiration flow path 9 likewise divides into two subsidiary paths 91, 92, which are attached via respective inlet valves 35, 45 to the respective fluid pumps 30, 40, specifically here to the respective pump chambers 31, 41. Here too, the pump chambers 31, 41 are separated from respective drive chambers 33, 43 by respective partition elements 32, 42. The partition elements 32, 42 have respective edges 34, 44, which are mounted fixedly in the respective fluid pump 30, 40. By way of respective outlet valves 36, 46 and subsidiary paths 93, 94 attached thereto, the aspiration fluid can then be removed via the aspiration fluid flow path 9. A third drive fluid 37 can be guided to the third drive chamber 33 with a third proportional valve 38. Correspondingly, a fourth drive fluid 47 can be guided to a fourth drive chamber 43 with a fourth proportional valve 48. The proportional valves 38, 48 are arranged in the panel 1. The deflection positions of the partition elements 32, 42 can be detected with respective deflection position sensors 39, 49. In the present case, the two fluid pumps 30, 40 are likewise operated alternately like the fluid pumps 10, 20.

FIG. 2 shows a schematic perspective representation of the panel 1 of the ophthalmic surgical system 100 according to FIG. 1. It is evident from FIG. 2 that the panel 1 has the cartridge accommodation region 56, which serves for the detachable arrangement of the cartridge 4. The panel 1 further has a drive fluid supply system 63, which serves to provide the respective drive fluid for the respective drive chambers 13, 23, 33, 43, the drive fluid being formed by air in the present case. The drive fluid supply system 63 has respective drive fluid sources 17, 27, 37, 47 (FIG. 1) for each of the fluid pumps 10, 20, 30, 40, said drive fluid sources being connected to respective proportional valves 18, 28, 38, 48. The drive fluid can be applied to the respective drive chamber 13, 23, 33, 43 by way of the proportional valves 18, 28, 38, 48 during intended operation.

It is further evident from FIG. 1 that each of the partition elements 12, 22, 32, 42 has a plate element 57 which is also deflected when a central region of the partition element 12, 22, 32, 42 is deflected. In the present case, the plate element 57 is designed as a metal plate and formed from a ferromagnetic substance. A thickness of the plate element 57 is smaller than a thickness of the partition element 12, 22, 32, 42.

The panel 1 further has a respective deflection position sensor 19, 29, 39, 49 for each of the fluid pumps 10, 20, 30, 40, the deflection position sensor in each case presently providing a sensor unit which uses a magnetic field in order to detect the position of the respective plate element 57 and hence of the respective partition element 12, 22, 32, 42.

FIG. 4 schematically shows a section of the cartridge 4 according to FIG. 3 arranged in the cartridge accommodation 56 of the panel 1 according to FIG. 2, to be precise in the region of the fluid pump 10. The following explanations are equally applicable to the fluid pumps 20, 30, 40. It is evident from FIG. 4 that the plate element 57 is arranged at a distance from an edging 58 of a housing (not labeled) of the cartridge 4 which holds the partition element 12.

The plate element 57 is provided on the drive chamber side of the partition element 12 such that the pump chamber 11 is arranged separated from the plate element 57 by the partition element 12. This is advantageous for reasons of sterility. To protect the plate element 57 from corrosion on account of an interaction with the drive fluid, the plate element 57 has a coating formed by a resin in the present case.

On the drive chamber side, the partition element 12 has a central accommodation region 59 for arranging the plate element 57, with a ring region 60 of the partition element 12 extending around the accommodation region 59 in the circumferential direction. In the present case, the accommodation region 59 is positioned in the central region of the partition element 12. This can ensure that the partition element 12 can be moved in substantially unimpeded fashion for an intended pump function.

To connect the partition element 12 to the plate element 57, provision is made in the present case for the partition element 12 to be provided on the drive chamber side with a connection element 61 for mechanically connecting the plate element 57 arranged in the accommodation region 59 to the partition element 12. In the present case, the connection element 61 is formed in the style of a frame which has a receiving groove 62 for an edge of the plate element 57. In particular, this makes it possible to easily remove the respective plate element 57 from the respective partition element 12, 22, 32, 42 once the cartridge 4 has been used, in order to be able to continue to use the substances separately.

However, a cohesive connection may also be provided in principle, in the case of which the plate element 57 is completely surrounded by a material of the partition element 12. By way of example, this can be implemented during the production of the partition element 12 by virtue of the plate element 57 being insert-molded into the substance, or the like. In principle, an adhesive connection may also be provided between the partition element 12 and the plate element 57. Naturally, these deliberations are equally applicable to the further fluid pumps 20, 30, 40 as well.

The partition element 12 is held in an edging 58 on a housing of the cartridge 4. The edging 58 not only seals the pump chamber 11 from the drive chamber 13 but also ensures reliable positioning of the partition element 12 during the intended operation of the fluid pump 10.

In the present case, the deflection position sensor 19 is in the form of an inductive sensor which, for example by using a substantially constant magnetic field, detects the position of the plate element 57 and transmits a corresponding sensor signal to a control device (not illustrated) of the panel 1. The control device of the panel 1 can evaluate this signal and can control the fluid pump 10 and the associated valves accordingly.

In this configuration, the partition element 12 has a geometry in the style of a circular panel. However, an at least partly polygonal contour may also be provided in alternative configurations. Thus, the plate element may also have a rectangular embodiment or the like.

In this configuration, the partition element 12 further has a bulge in an edge region that is the ring region 60. Proceeding from its edging 58, the partition element 12 therefore does not continue in planar fashion in the cross section, instead continuing in an arched manner, and so the partition element 12 has a plate-like embodiment in the cross section. This edge region 60 arched in plate-shaped fashion is advantageous since the partition element 12 can bulge out in the direction of an inner wall of the fluid chamber 11 when drive fluid is fed to the drive chamber 13 and can rest against the entirety of this inner wall in homogeneous fashion. Hence, the treatment fluid contained in the pump chamber 11 can be drained completely, and the pump chamber can be completely emptied. Hence, no residue of treatment fluid remains in the pump chamber 11, and so a maximally large conveying volume can be fed and removed. Additionally, what the edge region 60 arched like a plate achieves is that the plate element 57 is movable along the center axis of the partition element 12 with great accuracy and there is no wobble movement of the plate element 57. The partition element 12 is typically dimensioned such that a spring constant of less than 50 mmHg/10 mm is obtained.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Panel
2 Irrigation fluid container
3 Irrigation fluid
4 Cartridge
5 Surgical instrument
6 Eye
7 Crystalline lens
8 Irrigation fluid flow path
9 Aspiration flow path
10 Fluid pump
11 Pump chamber
12 Partition element
13 Drive chamber
14 Edge
15 Inlet valve
16 Outlet valve
17 Drive fluid source
18 Proportional valve
19 Deflection position sensor
20 Fluid pump
21 Pump chamber
22 Partition element

23 Drive chamber
24 Edge
25 Inlet valve
26 Outlet valve
27 Drive fluid source
28 Proportional valve
29 Deflection position sensor
30 Fluid pump
31 Pump chamber
32 Partition element
33 Drive chamber
34 Edge
35 Inlet valve
36 Outlet valve
37 Drive fluid source
38 Proportional valve
39 Deflection position sensor
41 Pump chamber
42 Partition element
43 Drive chamber
44 Edge
45 Inlet valve
46 Outlet valve
47 Drive fluid source
48 Proportional valve
49 Deflection position sensor
50 Membrane
51 Force sensor
52 Detection sensor
53 Aspiration fluid collection container
54 Adjustment mechanism
55 Coupling
56 Cartridge accommodation region
57 Metal plate
58 Edging
59 Accommodation region
60 Ring region
61 Connection element
62 Groove
63 Drive fluid supply system
81, 82, 83, 84, 91, 92, 93, 94 Subsidiary path
100 Ophthalmic surgical system

What is claimed is:

1. A cartridge for a panel of an ophthalmic surgical system for treating an eye, the cartridge being configured for insertion in a cartridge accommodation region of the panel, the cartridge comprising:

at least one fluid pump configured to convey a treatment fluid, the fluid pump having a pump chamber and a drive chamber separated from the pump chamber with a fluid-tight and ion-tight partition element that is at least regionally deflectable, wherein a drive fluid is feedable to the drive chamber and the treatment fluid is feedable to the pump chamber, wherein the partition element has at least one plate element made of an at least electrically conductive or at least ferromagnetic material, wherein the plate element is also deflected in case of a deflection of at least one region of the partition element and the plate element is spaced apart from an edging of the partition element that holds the partition element and is arranged in a central accommodation region of the partition element, with a ring region running around the accommodation region such that the partition element is in the form of a plate, wherein the partition element has at least one connection element located on the drive chamber side and serving for the mechanical connection of the plate element arranged in the accommodation region to the partition element, and wherein the at least one connection element partially overlaps the plate element on the drive chamber side.

2. The cartridge as claimed in claim 1, wherein a thickness of the plate element is smaller than a thickness of the partition element.

3. The cartridge as claimed in claim 1, wherein the plate element has a coating.

4. The cartridge as claimed in claim 1, wherein the at least one connection element has at least one receiving groove for an edge of the plate element.

5. A panel of an ophthalmic surgical system for treating an eye, the panel comprising:

a cartridge accommodation region configured to accommodate a cartridge having at least one fluid pump for conveying a treatment fluid, the fluid pump having a pump chamber and a drive chamber separated from the pump chamber with a partition element that is at least regionally deflectable, wherein a drive fluid is feedable to the drive chamber and the treatment fluid is feedable to the pump chamber;

a drive fluid supply system configured to feed the drive fluid into the drive chamber; and a sensor unit configured to detect a deflection position of the partition element, wherein the sensor unit is configured to use a magnetic field to detect a deflection position of the plate element which is part of a cartridge as claimed in claim 1 and arranged on the partition element.

6. An ophthalmic surgical system for treating an eye, the ophthalmic surgical system comprising:

a cartridge insertable in a cartridge accommodation region of a panel and having at least one fluid pump configured to convey a treatment fluid, the fluid pump having a pump chamber and a drive chamber separated from the pump chamber with a partition element that is at least regionally deflectable, wherein a drive fluid is feedable to the drive chamber and a treatment fluid is feedable to the pump chamber;

the panel which has the cartridge accommodation region for accommodating the cartridge, a drive fluid supply system configured to feed a drive fluid into the drive chamber and a sensor unit configured to detect a deflection position of the partition element; and an ophthalmic surgical handpiece for treating a crystalline lens of the eye, which can be coupled to the panel or the cartridge, wherein at least the cartridge is configured as claimed in claim 1.

7. The cartridge as claimed in claim 1, wherein the plate element is at least partially formed from a resilient substance.

8. The cartridge as claimed in claim 1, wherein the cartridge is configured to be detachably connected to the panel.

* * * * *